(12) United States Patent
Sun et al.

(10) Patent No.: US 8,717,559 B2
(45) Date of Patent: May 6, 2014

(54) OPTICAL FIBER PROBE AND RAMAN DETECTING SYSTEM HAVING SAME

(75) Inventors: Ying-Hui Sun, Beijing (CN); Kai Liu, Beijing (CN); Kai-Li Jiang, Beijing (CN); Shou-Shan Fan, Beijing (CN)

(73) Assignees: Tsinghua University, Beijing (CN); Hon Hai Precision Industry Co., Ltd., New Taipei (TW)

( * ) Notice: Subject to any disclaimer, the term of this patent is extended or adjusted under 35 U.S.C. 154(b) by 289 days.

(21) Appl. No.: 12/961,316

(22) Filed: Dec. 6, 2010

(65) Prior Publication Data

US 2012/0062880 A1 Mar. 15, 2012

(30) Foreign Application Priority Data

Sep. 10, 2010 (CN) .......................... 2010 1 0278288

(51) Int. Cl.
*G01J 3/00* (2006.01)
*G01J 3/44* (2006.01)

(52) U.S. Cl.
USPC .......................................... 356/301; 356/300

(58) Field of Classification Search
USPC ................................. 356/300, 301
See application file for complete search history.

(56) References Cited

U.S. PATENT DOCUMENTS

| | | | | |
|---|---|---|---|---|
| 4,883,561 A * | 11/1989 | Gmitter et al. | ................... | 438/27 |
| 5,327,211 A * | 7/1994 | Carron et al. | ................... | 356/301 |
| 5,864,397 A * | 1/1999 | Vo-Dinh | ................... | 356/301 |
| 7,733,479 B2 * | 6/2010 | Shew et al. | ................... | 356/244 |
| 8,048,256 B2 * | 11/2011 | Feng et al. | ................... | 156/305 |
| 8,269,169 B1 * | 9/2012 | Sinton et al. | ................... | 250/338.1 |
| 2005/0113658 A1 * | 5/2005 | Jacobson et al. | ................... | 600/342 |
| 2005/0148003 A1 * | 7/2005 | Keith et al. | ................... | 435/6 |
| 2006/0038990 A1 * | 2/2006 | Habib et al. | ................... | 356/301 |
| 2008/0192247 A1 * | 8/2008 | Zerbi et al. | ................... | 356/301 |
| 2008/0198376 A1 * | 8/2008 | Poponin | ................... | 356/301 |
| 2009/0008712 A1 * | 1/2009 | Choi et al. | ................... | 257/347 |
| 2009/0181239 A1 * | 7/2009 | Fan et al. | ................... | 428/327 |
| 2010/0259752 A1 * | 10/2010 | Shah et al. | ................... | 356/300 |
| 2010/0297686 A1 * | 11/2010 | Gogotsi et al. | ................... | 435/29 |

OTHER PUBLICATIONS

Y Sun et al., "Highly Sensitive Surface-Enhanced Raman Scattering Substrate Made from Superaligned Carbon Nanotubes", Apr. 13, 2010; Nano Lett. 10, 1747-1753.*

Chen et al. J. Phy. Chem. C (2007), 111, 16167-16173.*

* cited by examiner

*Primary Examiner* — Gregory J Toatley
*Assistant Examiner* — Hina F Ayub
(74) *Attorney, Agent, or Firm* — Novak Druce Connolly Bove + Quigg LLP (57) ABSTRACT

An optical fiber probe includes an optical fiber, a carbon nanotube film structure, and a number of metallic particles. The optical fiber includes a detecting end. The carbon nanotube film structure is located on a surface of the detecting end. The carbon nanotube film structure includes a number of carbon nanotubes joined by van der Waals attractive force therebetween. The metallic particles are located on outer surfaces of the carbon nanotubes.

19 Claims, 14 Drawing Sheets

OPTICAL FIBER PROBE AND RAMAN DETECTING SYSTEM HAVING SAME

CROSS-REFERENCE TO RELATED APPLICATION

This application claims all benefits accruing under 35 U.S.C. §119 from China Patent Application No. 201010278288.0, filed on 2010/9/10, in the China Intellectual Property Office, the disclosure of which is incorporated herein by reference.

BACKGROUND

1. Technical Field

The present disclosure relates to an optical fiber probe and a Raman detecting system having the optical fiber probe.

2. Description of Related Art

An optical fiber probe for detecting Raman signals generally includes an optical fiber, and a plurality of silver particles located on a detecting end of the optical fiber. The optical fiber probe can be manufactured by depositing the silver particles on a surface of the detecting end. The silver particles generally are deposited on the surface of the detecting end by, for example, e-beam evaporation or sputtering. Thus, the silver particles are located on the surface of the detecting end firmly to form an integrated structure.

However, if the silver particles are damaged by a mechanical force, or are eroded by a reagent, it is hard to just remove the silver particles from the surface of the detecting end, and keep the optical fiber from not being damaged. Thus, it is difficult to recover the optical fiber from the optical fiber probe.

What is needed, therefore, is to provide an optical fiber probe, and a detecting system having the optical fiber prober, to overcome the above-described shortcomings.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings. It should be noted that references to "an" or "one" embodiment in this disclosure are not necessarily to the same embodiment, and such references mean at least one.

One embodiment of a Raman detecting system includes a projecting module, an optical fiber probe, and a receiving module. The optical fiber probe includes an optical fiber, and a composite carbon nanotube film positioned on an end of the optical fiber.

The projecting module projects a beam of light onto the composite carbon nanotube film. The beam of light is directly projected onto the composite carbon nanotube film, or enters the optical fiber from an end of the optical fiber, and then it is transmitted onto the composite carbon nanotube film. Scattering light can be formed by irradiating a sample adhered on the composite carbon nanotube film by the beam of light. The scattering light can enter the optical fiber and be transmitted to the receiving module. Area of a cross section of the beam of light on the composite carbon nanotube film can be less than or equal to 6 square centimeters. The projecting module can include a light source such as an argon laser. A frequency width of the argon laser can be narrower than a frequency width of other light source. The beam of light can have a wavelength of about 450.0 nanometers to about 514.5 nanometers. In one embodiment, the wavelength of the beam of light is about 514.5 nanometers.

The receiving module collects the scattering light scattered by the composite carbon nanotube film, to create a Raman spectra figure of the sample adhered on the composite carbon nanotube film. The receiving module can include a multi-channel photon detector such as a charge coupled device (CCD), or a single-channel photon detector such as a photomultiplier. Details of vibration modes of the sample can be read from the Raman spectra figure formed by the receiving module.

The sample can be solid, liquid, or gaseous. The solid sample can be powders, or particles with the sample adhered thereon. The liquid sample can be drops dissolving the sample therein, or molten sample. The gaseous sample can be the sample volatilized in air or in a chamber. The solid sample and the liquid sample can be directly adhered to the composite carbon nanotube film. The gaseous sample can be absorbed in the composite carbon nanotube film. When the composite carbon nanotube film is irradiated by the beam of light, a part of the beam of light can strike the sample to form the scattering light. Specifically, some photons of the beam of light can strike the sample and collide with molecules of the sample, thus, the momentum or the frequency of the photons can be changed. The vibration of the frequency of the photons can correspond to vibration frequencies of chemical bonds in the molecules of the sample. Thus, the molecular structure can be read from the scattering light.

The optical fiber can be a single-mode fiber or a multimode fiber. The optical fiber can include a detecting end and a measuring end. The detecting end and the measuring end can be two opposite ends of the optical fiber. The measuring end can be optically connected to the receiving module. The scattering light can enter the optical fiber from the detecting end and be transmitted to the measuring end, and enter the receiving module via the measuring end. The measuring end can also be optically connected to the projecting module. The projecting module projects the beam of light to the measuring end. The beam of light can enter the optical fiber from the measuring end and be transmitted to the detecting end. Thus, the composite carbon nanotube film can be irradiated.

The composite carbon nanotube film can be positioned on the surface of the detecting end. In one embodiment, the composite carbon nanotube film is wrapped about the detecting end. The composite carbon nanotube film can include a carbon nanotube film structure and a metallic film located on a surface of the carbon nanotube film structure.

The carbon nanotube film structures can include a structure wherein a plurality of carbon nanotubes positioned on the surface of the detecting end that are substantially perpendicular to the surface of the detecting end. In one such structure, the carbon nanotubes can be applied to the detecting end by forming an array on the detecting end. The array can be formed by means of a MOCVD (Metal-organic Chemical Vapor Deposition) method, or an electrophoresis method. The carbon nanotubes can be substantially parallel to the surface of the detecting end, thus, the carbon nanotubes can be substantially parallel to the surface of the carbon nanotube film structure. In one embodiment, the carbon nanotube film structure is capable of forming a free-standing structure. The term "free-standing structure" can be defined as a structure that does not have to be supported by a substrate. For example, a free-standing structure can sustain the weight of itself when it is hoisted by a portion thereof without any significant damage to its structural integrity. The free-standing structure of the carbon nanotube film structure is realized by the carbon nanotubes joined by van der Waals attractive force. So, if the carbon nanotube film structure is placed between two separate supporters, a portion of the carbon nanotube film structure, not in contact with the two supporters, would be suspended between the two supporters and yet maintain film structural integrity.

The carbon nanotube film structure includes a plurality of carbon nanotubes uniformly distributed therein, and joined by van der Waals attractive force therebetween. The carbon nanotubes in the carbon nanotube film structure can be orderly or disorderly arranged. The term 'disordered carbon nanotube film structure' includes, but is not limited to, a structure where the carbon nanotubes are arranged along many different directions, such that the number of carbon nanotubes arranged along each different direction can be almost the same (e.g. uniformly disordered), and/or entangled with each other. 'Ordered carbon nanotube film structure' includes, but is not limited to, a structure where the carbon nanotubes are arranged in a consistently systematic manner, e.g., the carbon nanotubes are arranged approximately along a same direction and or have two or more sections within each of which the carbon nanotubes are arranged approximately along a same direction (different sections can have different directions). The carbon nanotubes in the carbon nanotube film structure can be single-walled, double-walled, and/or multi-walled carbon nanotubes.

Macroscopically, the carbon nanotube film structure may have a substantially planar structure. The planar carbon nanotube structure can have a thickness of about 0.5 nanometers to about 100 microns. Microscopically, the carbon nanotube film structure includes a plurality of carbon nanotubes and defines a plurality of micropores having a size of about 1 nanometer to about 500 nanometers. Therefore, the carbon nanotube film structure 11 has a nanoporous microstructure. The carbon nanotube film structure includes at least one carbon nanotube film, the at least one carbon nanotube film including a plurality of carbon nanotubes substantially parallel to a surface of the corresponding carbon nanotube film.

Figure 1:
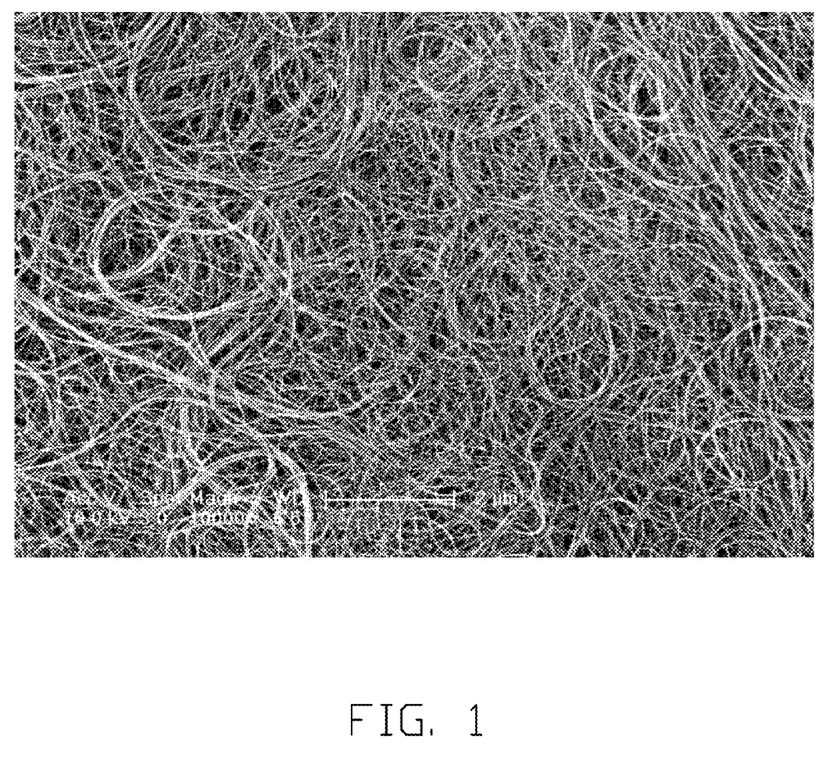
FIG. 1 shows a Scanning Electron Microscope (SEM) image of a flocculated carbon nanotube film.

The carbon nanotube film structure can include a flocculated carbon nanotube film as shown in FIG. 1. The flocculated carbon nanotube film can include a plurality of long, curved, disordered carbon nanotubes entangled with each other and can form a free-standing structure. Further, the flocculated carbon nanotube film can be isotropic. The carbon nanotubes can be substantially uniformly dispersed in the carbon nanotube film. The adjacent carbon nanotubes are acted upon by the van der Waals attractive force therebetween, thereby forming an entangled structure with micropores defined therein. Alternatively, the flocculated carbon nanotube film is very porous. Sizes of the micropores can be of about 1 nanometer to about 500 nanometers. Further, due to the carbon nanotubes in the carbon nanotube structure being entangled with each other, the carbon nanotube structure employing the flocculated carbon nanotube film has excellent durability, and can be fashioned into desired shapes with a low risk to the integrity of carbon nanotube structure. The flocculated carbon nanotube film, in some embodiments, will not require the use of structural support or due to the carbon nanotubes being entangled and adhered together by van der Waals attractive force therebetween. The flocculated carbon nanotube film can have a thickness of about 0.5 nanometers to about 100 microns, and can define a plurality of micropores having a diameter of about 1 nanometer to about 500 nanometers. The micropores defined in the flocculated carbon nanotube film can increase the specific surface area of the flocculated carbon nanotube film. Thus, more of the sample can be accommodated in the flocculated carbon nanotube film.

Figure 2:
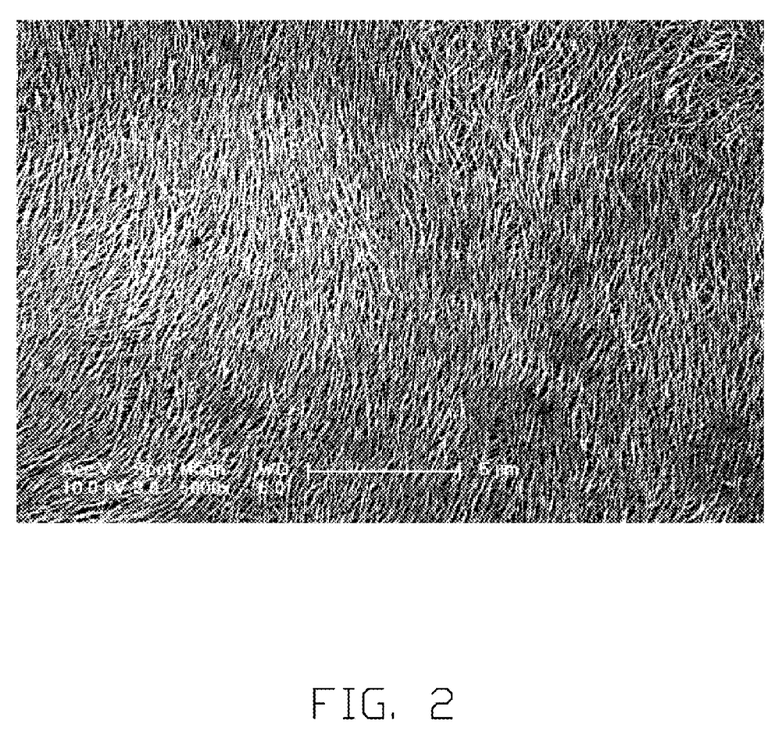
FIG. 2 shows an SEM image of a pressed carbon nanotube film.

The carbon nanotube film structure can include a pressed carbon nanotube film. The carbon nanotubes in the pressed carbon nanotube film can be arranged along a same direction or arranged along different directions. The carbon nanotubes in the pressed carbon nanotube film can rest upon each other. The adjacent carbon nanotubes are combined and attracted to each other by van der Waals attractive force, and can form a free-standing structure. An angle between a primary alignment direction of the carbon nanotubes and a surface of the pressed carbon nanotube film can be in an approximate range from 0 degrees to approximately 15 degrees. The pressed carbon nanotube film can be formed by pressing a carbon nanotube array. The angle is closely related to pressure applied to the carbon nanotube array. The greater the pressure, the smaller the angle. The carbon nanotubes in the carbon nanotube film can be substantially parallel to the surface of the carbon nanotube film when the angle is 0 degrees. A length and a width of the carbon nanotube film can be set as desired. The pressed carbon nanotube film can include a plurality of carbon nanotubes substantially aligned along one or more directions. The pressed carbon nanotube film can be obtained by pressing the carbon nanotube array with a pressure head. Alternatively, the shape of the pressure head and the pressing direction can determine the direction of the carbon nanotubes arranged therein. Specifically, in one embodiment, when a planar pressure head is used to press the carbon nanotube array along the direction perpendicular to a substrate. A plurality of carbon nanotubes pressed by the planar pressure head may be sloped in many directions. In another embodiment, as shown in FIG. 2, when a roller-shaped pressure head is used to press the carbon nanotube array along a certain direction, the pressed carbon nanotube film having a plurality of carbon nanotubes substantially aligned along the certain direction can be obtained. In another embodiment, when the roller-shaped pressure head is used to press the carbon nanotube array along different directions, the pressed carbon nanotube film having a plurality of carbon nanotubes substantially aligned along different directions can be obtained. The pressed carbon nanotube film can have a thickness of about 0.5 nanometers to about 100 microns, and can define a plurality of micropores having a diameter of about 1 nanometer to about 500 nanometers. The micropores defined in the pressed carbon nanotube film can increase the specific surface area of the pressed carbon nanotube film. Thus, more of the sample can be accommodated in the pressed carbon nanotube film.

Figure 3:
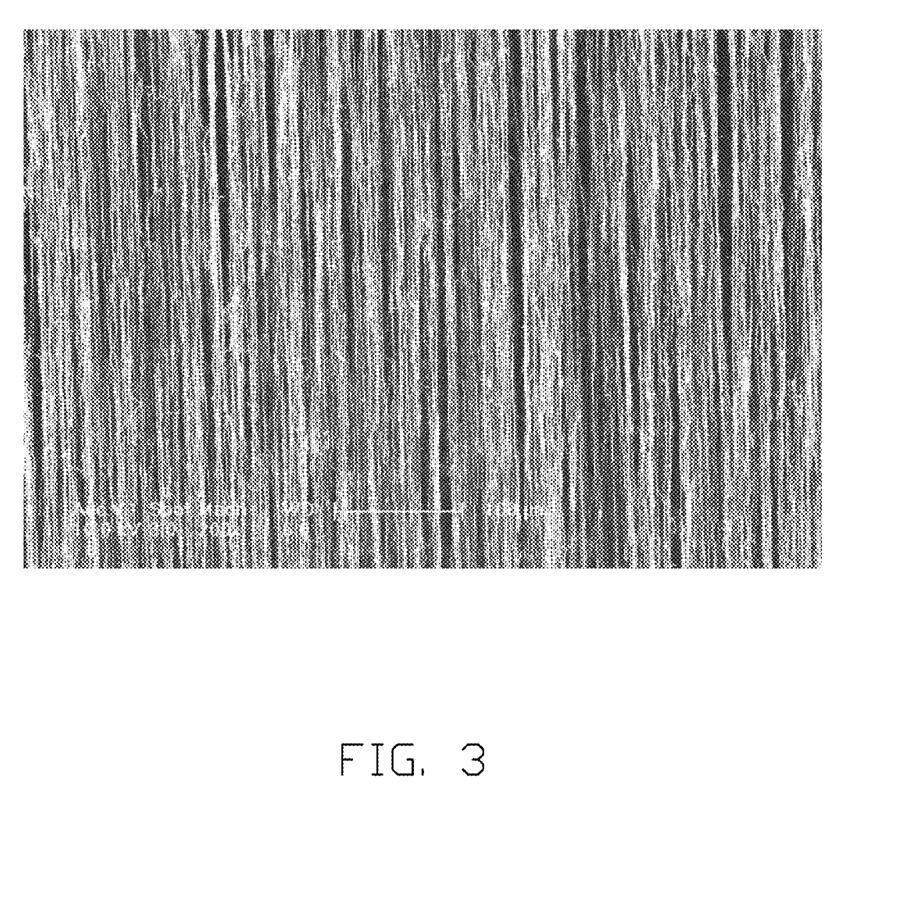
FIG. 3 shows an SEM image of a drawn carbon nanotube film.

In some embodiments, the carbon nanotube film structure includes at least one drawn carbon nanotube film as shown in FIG. 3. A transmittance of the drawn carbon nanotube film substantially greater than about 75 percent. The drawn carbon nanotube film can have a thickness of about 0.5 nanometers to about 100 microns. The drawn carbon nanotube film includes a plurality of carbon nanotubes that can be arranged substantially parallel to a surface of the drawn carbon nanotube film. A plurality of micropores having a size of about 1 nanometer to about 500 nanometers can be defined by the carbon nanotubes. A large number of the carbon nanotubes in the drawn carbon nanotube film can be oriented along a preferred orientation, meaning that a large number of the carbon nanotubes in the drawn carbon nanotube film are arranged substantially along the same direction. An end of one carbon nanotube is joined to another end of an adjacent carbon nanotube arranged substantially along the same direction, by van der Waals attractive force. More specifically, the drawn carbon nanotube film includes a plurality of successively oriented carbon nanotube segments joined end-to-end by van der Waals attractive force therebetween. Each carbon nanotube segment includes a plurality of carbon nanotubes substantially parallel to each other, and joined by van der Waals attractive force therebetween. The carbon nanotube segments can vary in width, thickness, uniformity and shape. A small number of the carbon nanotubes are randomly arranged in the drawn carbon nanotube film, and has a small if not negligible effect on the larger number of the carbon nanotubes in the drawn carbon nanotube film arranged substantially along the same direction. The carbon nanotube film is capable of forming a free-standing structure. The term "free-standing structure" can be defined as a structure that does not have to be supported by a substrate. For example, a free-standing structure can sustain the weight of itself when it is hoisted by a portion thereof without any significant damage to its structural integrity. The free-standing structure of the drawn carbon nanotube film is realized by the successive segments joined end to end by van der Waals attractive force.

Figure 4:
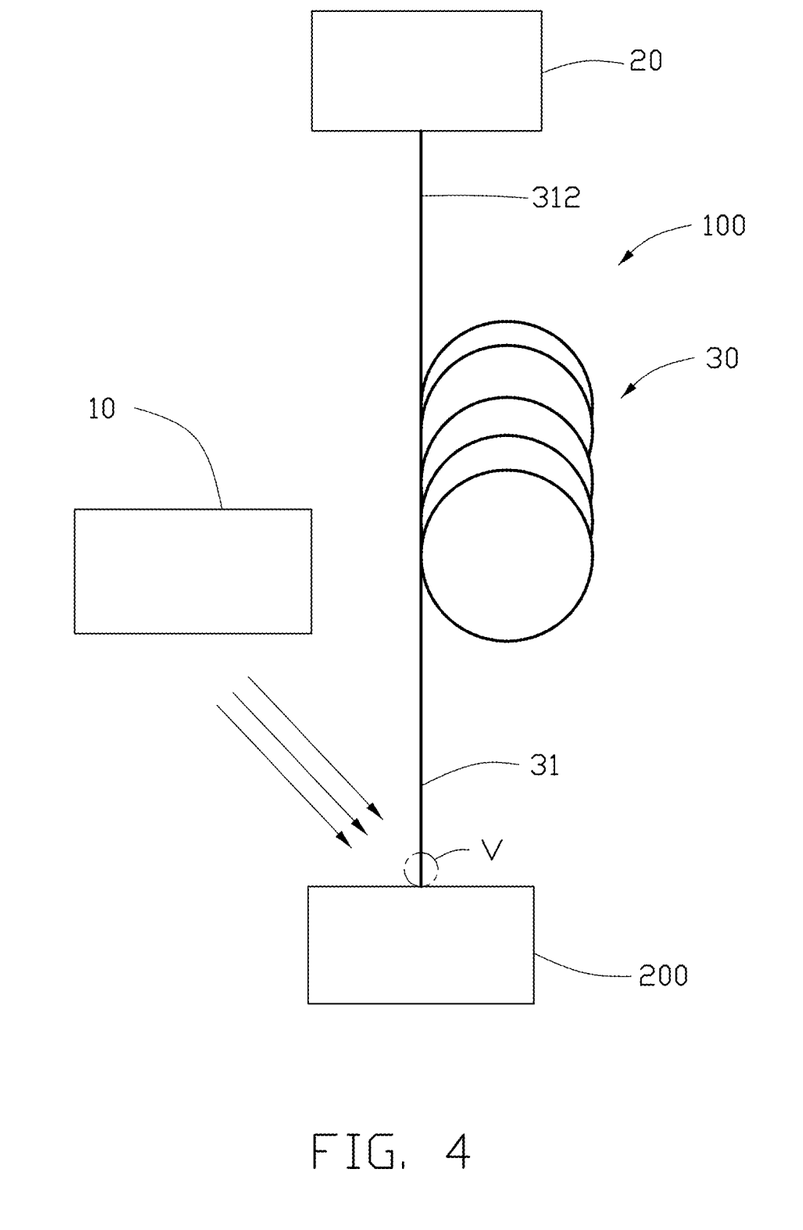
FIG. 4 is a schematic structural view of one embodiment of a Raman detecting system.

Understandably, some vibration can occur in the orientation of the carbon nanotubes in the drawn carbon nanotube film as can be seen in FIG. 4. Microscopically, the carbon nanotubes oriented substantially along the same direction may not be perfectly aligned in a straight line, and some curve portions may exist. Furthermore, it can be understood that some carbon nanotubes are located substantially side by side and oriented along the same direction and in contact with each other.

The carbon nanotube film structure can include a plurality of stacked drawn carbon nanotube films. The number of the layers of the drawn carbon nanotube films is not limited, provided the thickness of the carbon nanotube film structure can be maintained in a range from about 0.5 nanometers to about 100 microns. In one embodiment, the carbon nanotube film structure includes at least four layers of drawn carbon nanotube films, and the transmittance of the carbon nanotube film structure is substantially greater than about 40 percent. Adjacent drawn carbon nanotube films can be adhered to each other by only the van der Waals attractive force therebetween (e.g. no adhesives required). An angle can exist between the carbon nanotubes in adjacent drawn carbon nanotube films. The angle between the aligned directions of the adjacent drawn carbon nanotube films can range from 0 degrees to about 90 degrees. In one embodiment, the angle between the aligned directions of the adjacent drawn carbon nanotube films is substantially 90 degrees. Simultaneously, aligned directions of adjacent carbon nanotube films are substantially perpendicular to each other, thus a plurality of micropores and nodes can be defined by the carbon nanotube film structure. The carbon nanotube film structure includes a plurality of uniform micropores and nodes, thereby forming a nanoporous structure. The nanoporous structure can provide a huge surface area to adsorb more of the sample therein.

The metallic film can be located on one surface of the carbon nanotube film structure or on two opposite surfaces of the carbon nanotube film structure. The metallic film can be formed by means of depositing a metallic material on the carbon nanotube film structure via e-beam evaporation or sputtering. A quartz crystal oscillator can be used to monitor the film thickness. A material of the metallic film can be noble metal or transition metal. The material of the metallic film can be gold, silver, copper, or nickel. The metallic film can have a thickness of about 1 nanometer to about 45 nanometers. In one embodiment, the metallic film has a thickness of about 5 nanometers.

Microscopically, the metallic film can include a plurality of metallic particles. The metallic particles can be located on the outer surfaces of the carbon nanotubes of the carbon nanotube film structure. Simultaneously, the metallic particles can be located on outer surfaces of all of the carbon nanotubes, or can be located on outer surfaces of part of the carbon nanotube film structure. Generally, more metallic particles will be located on the carbon nanotubes on the exterior of the carbon nanotube film structure. The greater the thickness of the metallic film, the greater an average diameter of the metallic particles. The average diameter of the particles can be about 5 nanometers to about 50 nanometers, if the thickness of the metallic film is about 1 nanometer to about 45 nanometers. In one embodiment, the average diameter of the particles is about 18 nanometers to 22 nanometers. A plurality of interparticle gaps can be defined among the metallic particles. An average interparticle gap can be about 1 nanometer to about 15 nanometers. In other words, an average gap or an average space between the metallic particles can be about 1 nanometer to about 15 nanometers. In one embodiment, the average interparticle gap is about 2 nanometers to about 5 nanometers. Less than 1 percent of the metallic particles can be greater than 50 nanometers. Less than 1 percent of the interparticle gap can be greater than 15 nanometers.

The composite carbon nanotube film can further include a transition layer sandwiched between the carbon nanotube film structure and the metallic film. The transition layer can be deposited on the carbon nanotube film structure before the evaporation or sputtering of the metallic film. The transition layer can have a thickness of about 10 nanometers to about 100 nanometers. In one embodiment, the transition layer has a thickness of about 15 nanometers to about 30 nanometers.

Microscopically, the transition layer can cover part or all the outer surfaces of the carbon nanotubes of the carbon nanotube film structure. The transition layer can provide a surface smoother than the surface of the carbon nanotube film structure. Stresses endured by the metallic particles in all orientations can be substantially equal to each other. Thus, the transition layer can improve the shape regularity of the metallic particles. The metallic particles can tend to form quasi-uniform spheres on the transition layer and increase electromagnetic enhancement and Raman enhancement factor of the SERS substrate 120. A material of the transition layer can be inorganic oxide such as silicon dioxide and magnesium oxide. In one embodiment, the transition layer is a silicon dioxide layer with a thickness of about 20 nanometers.

The method for fabricating the optical fiber probe is not limited, provided the composite carbon nanotube film can be positioned on the surface of the detecting end. The composite carbon nanotube film can be configured to be a soft Raman scattering substrate assembled on the optical fiber. The optical probe can be formed by the following steps: depositing or coating the metallic film on the surface of the carbon nanotube film to form the composite carbon nanotube film; and adhering or wrapping the composite carbon nanotube film on the detecting end. If the carbon nanotube film structure is not a free-standing structure, the optical fiber probe can also be formed by the following steps: coating or growing a plurality of carbon nanotubes on the detecting end to form the carbon nanotube film; and depositing or coating the metallic film on the surface of the carbon nanotube film to form the composite carbon nanotube film. The composite carbon nanotube film can be adhered to the detecting end by glue, or just by van der Waals attractive force.

A light splitter module can be introduced to the Raman detecting system to harmonize the beam of light and the scattering light, when the projecting module is optically connected to the measuring end. In one embodiment, the measuring end can be connected to a first end of the light splitter module, and both the projecting module and the receiving module can be connected to a second end of the light splitter module. When the beam of light is projected by the projected module, the beam of light enters the splitter module from the second end and is transmitted to the first end of the splitter module other than the receiving module. The beam of light through the splitter module can enter the optical fiber from the measuring end and be transmitted to the detecting end. Thus, the composite carbon nanotube film having the sample thereon can be irradiated by the beam of light to form the scattering light. The scattering light can enter the optical fiber from the detecting end and be transmitted to the measurement end. The scattering light through the optical fiber can enter the splitter module from the second end of the splitter module to the receiving module rather than the projecting module.

The metallic particles are located on the carbon nanotube film structure other than directly located on the surface of the optical fiber, thus, the metallic particles and the optical fiber will not be adhered together to form an integrated structure. Typically, the optical fiber will be damaged if the metallic particles directly adhered to optical fiber probe are removed from the optical fiber probe. The carbon nanotube film structure can be adhered to the detecting end by glue or adhesive nature of the carbon nanotube film structure. Thus, the carbon nanotube film structure can be removed from the optical fiber probe by scrubbing the optical fiber probe with a cloth, an eraser, or a lens paper without damage to the optical fiber. Therefore, the optical fiber of the optical fiber probe can be recovered from the optical fiber probe easily. Further, the sample adhered on the metallic particles can be removed from the optical fiber by removing the composite carbon nanotube film adhered on the optical fiber, or by replacing the composite carbon nanotube film with a new composite carbon nanotube film without sample. Therefore, the optical fiber can be configured to detecting a plurality of samples. However, the sample will be hard to remove from the optical fiber, if the metallic particles directly are adhered to optical fiber probe.

The carbon nanotubes of the composite carbon nanotube film can define a plurality of uniform micropores. Thus, the metallic particles having small average size can be formed on the carbon nanotube film structure to define a plurality of interparticle gaps with a small average size. The smaller the average size of the interparticle gap, the greater the electromagnetic enhancement and Raman enhancement factor of the optical fiber probe.

Referring to FIG. 4, one embodiment of a Raman detecting system 100 can be shown to illustrate the disclosure in detail.

The Raman detecting system 100 includes a projecting module 10, a receiving module 20, and an optical fiber probe 30. The projecting module 10 and the receiving module 20 can be located on opposite ends of the optical fiber probe 30. An end of the optical fiber probe 30 can extend into a sample 200, absorb the sample 200, and detect Raman signals of the sample 200.

A beam of light can be projected by the projecting module 10 to irradiate the sample 200 absorbed on the optical fiber probe 30. Some photons of the beam of light can strike the sample 200 and collide with molecules of the sample, thus, the momentum or the frequency of the photons can be changed. Thus, a scattering light including the photons can be produced by irradiating the sample 200 absorbed on the optical fiber probe 30 by the beam of light. The scattering light can enter the optical fiber probe 30, form the sample 200 and be transmitted to the receiving module 20.

Figure 5:
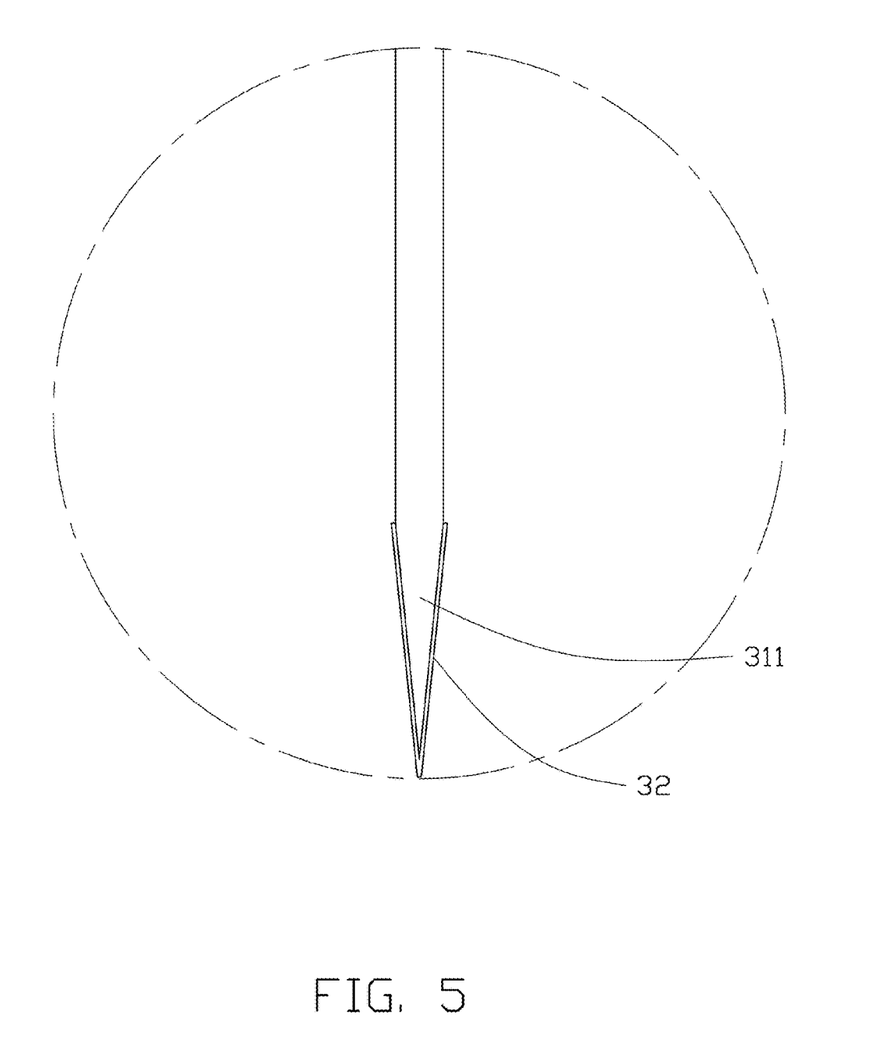
FIG. 5 is a local magnifying schematic structural view of the Raman detecting system in FIG. 4.

Referring to FIG. 4 and FIG. 5, the optical fiber probe 30 includes an optical fiber 31 and a composite carbon nanotube film 32 positioned on the optical fiber 31. The optical fiber 31 can include a detecting end 311 and a measuring end 312. A shape of the detecting end 311 is not limited. In one embodiment, the shaped of the detecting end 311 is a cone. A diameter of the cone can be gradually increased from the first end to the second end.

Figure 6:
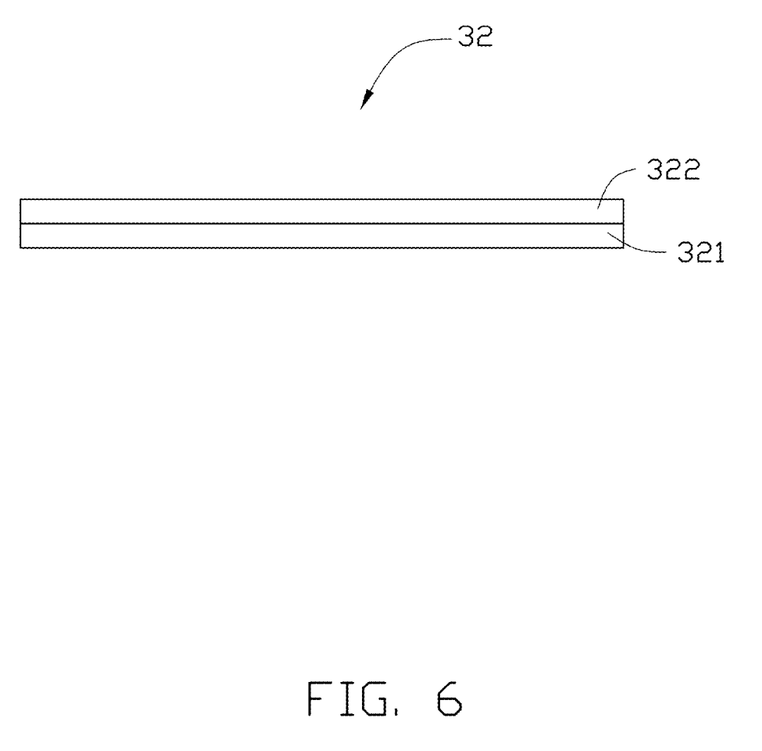
FIG. 6 is a schematic structural view of one embodiment of a composite carbon nanotube film.

The composite carbon nanotube film 32 can be a free-standing structure and be wrapped about the surface of the detecting end 311. The composite carbon nanotube film 32 can be adhered to the surface of the detecting end 311 by transparent glue, or adhesive nature of the composite carbon nanotube film 32. Referring to FIG. 6, the composite carbon nanotube film 32 can include a carbon nanotube film structure 321 and a metallic film 322 located on the carbon nanotube film structure 321. The metallic film 322 can be located on one or both surfaces. In one embodiment, the metallic film 322 is positioned on the first surface.

Figure 7:
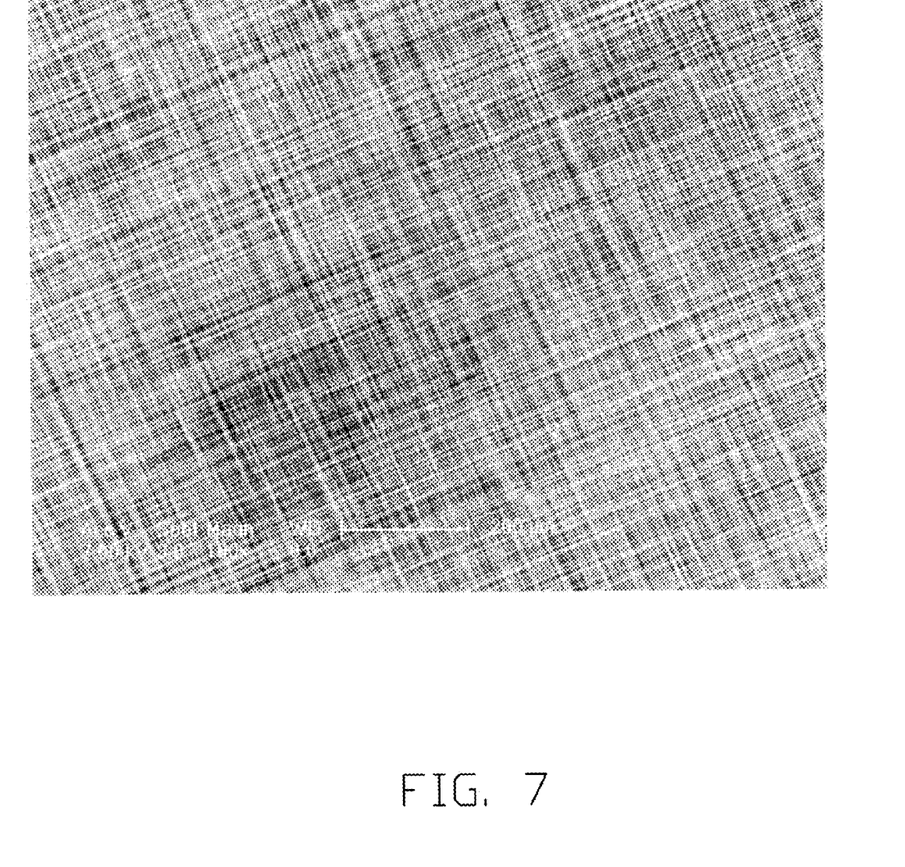
FIG. 7 shows an SEM image of a carbon nanotube film structure consisting of a plurality of stacked drawn carbon nanotube films defined as a CNT grid.

Referring to FIG. 7, the carbon nanotube film structure 321 includes a plurality of stacked drawn carbon nanotube films. Aligned directions of carbon nanotubes of adjacent drawn carbon nanotube films can be substantially perpendicular to each other. The carbon nanotube film structure 321 can be defined as a CNT grid.

Figure 8:
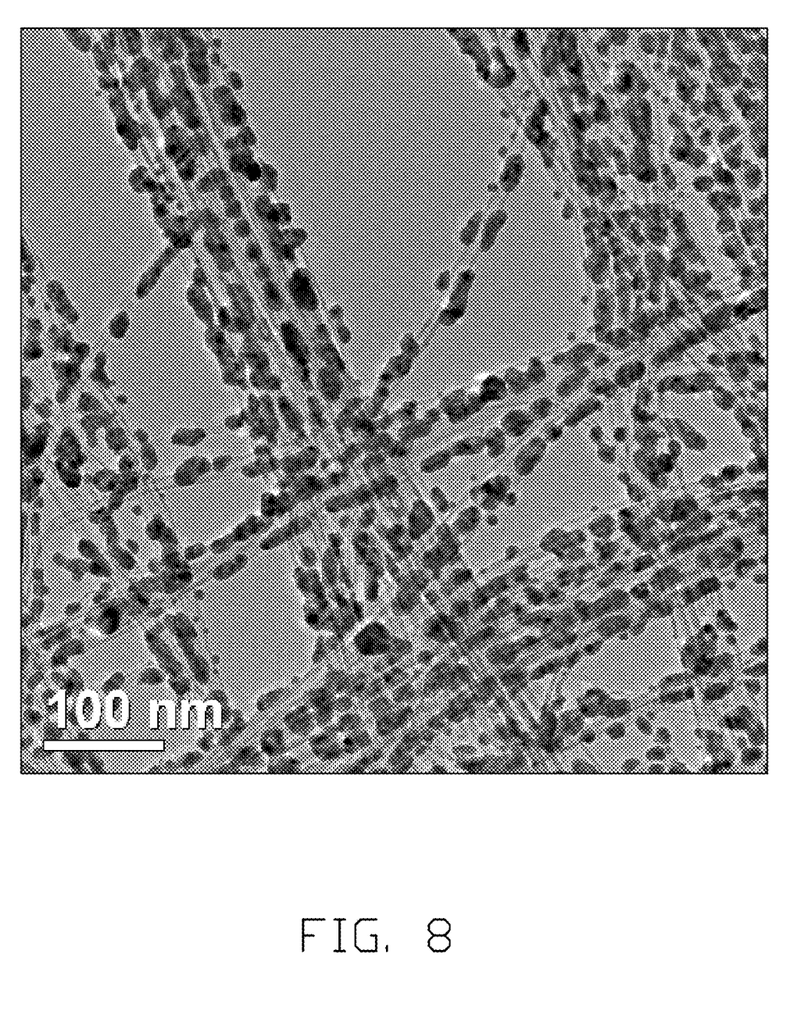
FIG. 8 shows a low magnification Transmission Electron Microscope (TEM) image of a composite carbon nanotube film defined as an Ag-CNT grid.
Figure 9:
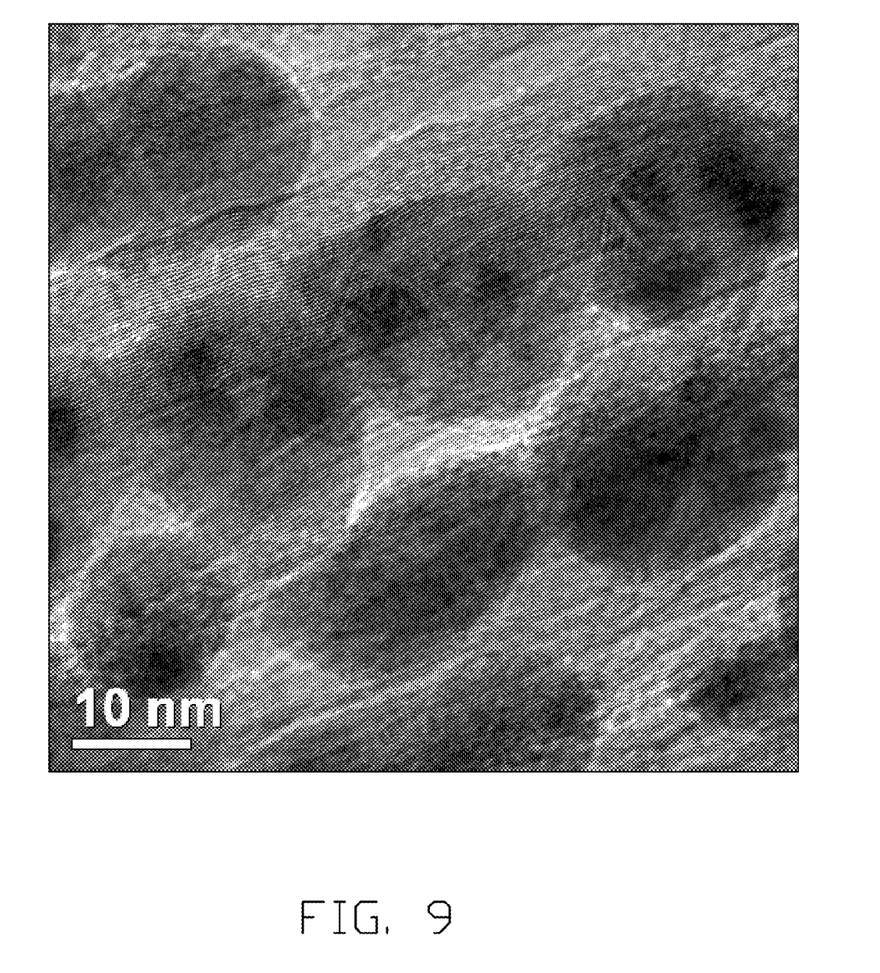
FIG. 9 shows a high magnification TEM image of the composite carbon nanotube film in FIG. 8.
Figure 10:
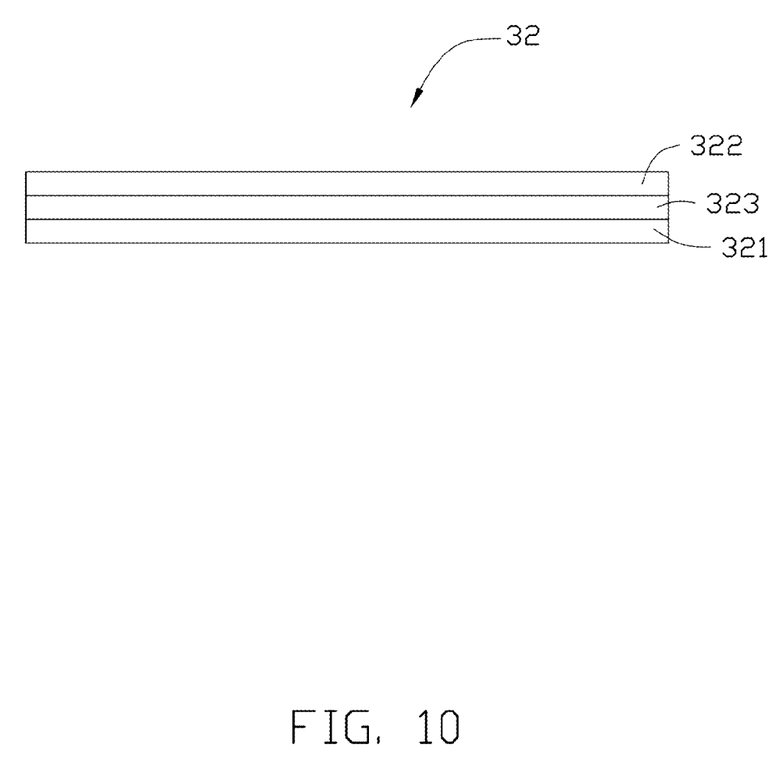
FIG. 10 is a schematic structural view of one embodiment of a composite carbon nanotube film.
Figure 11:
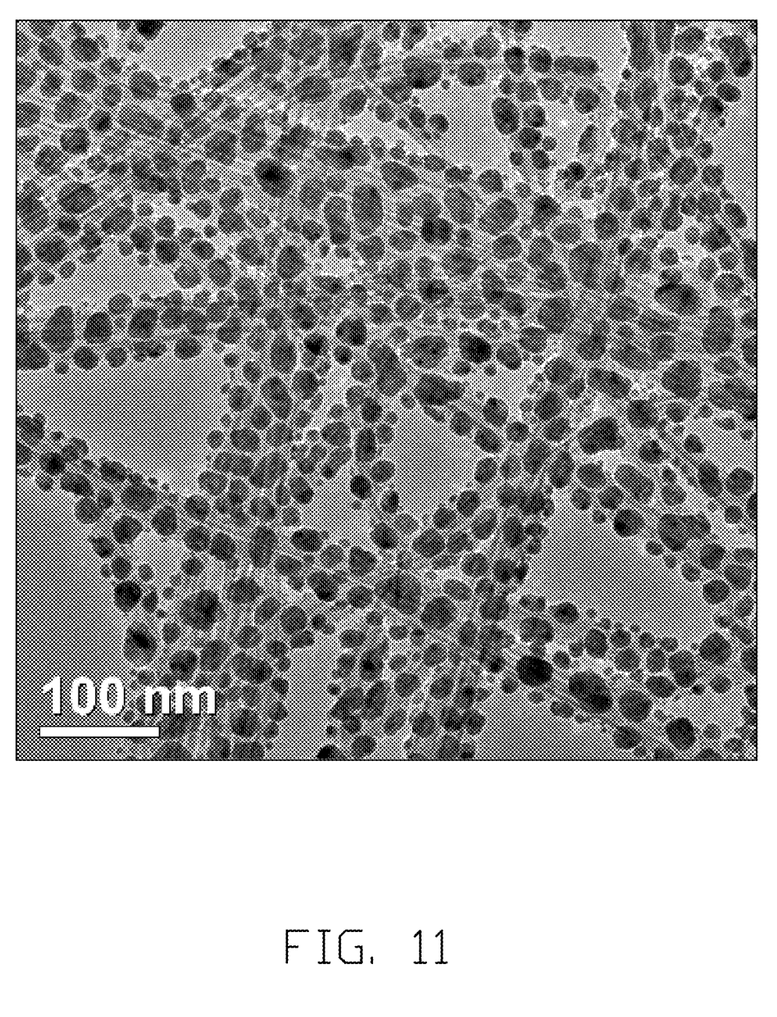
FIG. 11 shows a low magnification TEM image of a composite carbon nanotube film defined as an Ag—$SiO_2$-CNT grid
Figure 12:
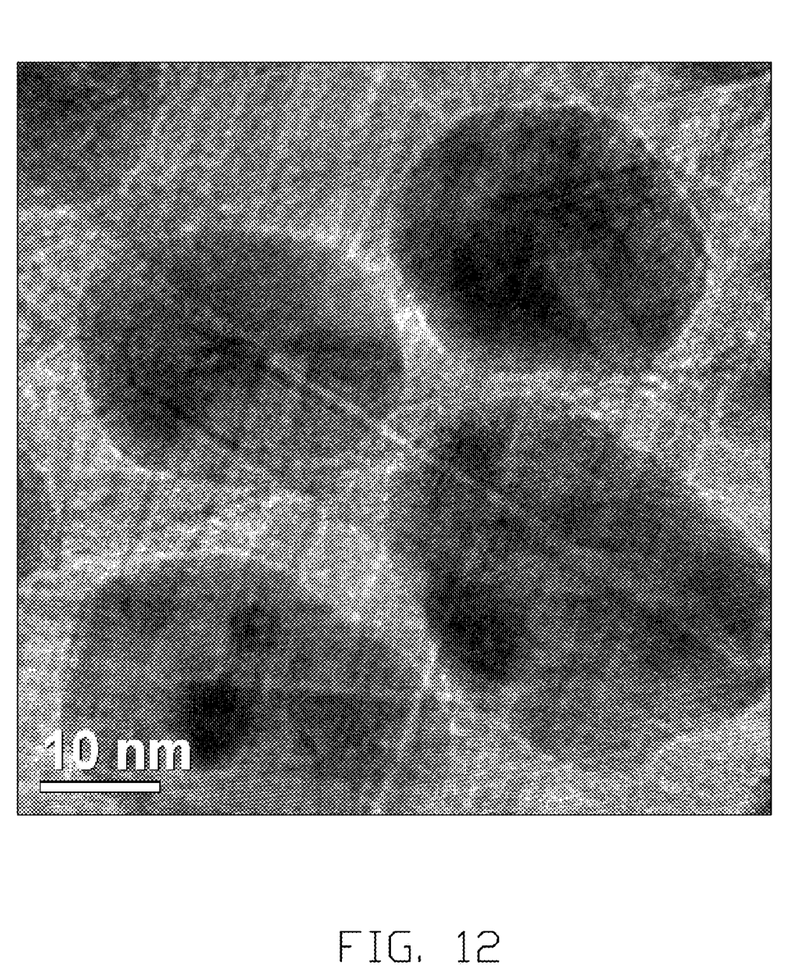
FIG. 12 shows a high magnification TEM image of the composite carbon nanotube film in FIG. 11.

The metallic film 322 can be a silver film having a thickness of about 5 nanometers. Referring to FIG. 8 and FIG. 9, the composite carbon nanotube film 32 including the CNT grid and the silver film can be defined as an Ag-CNT grid. The silver film can be located on a surface of the CNT grid, and have a thickness of about 5 nanometers. Microscopically, an average diameter of silver particles of the silver film can be substantially 20 nanometers. Referring to FIG. 10, FIG. 11 and FIG. 12, a transition layer 323 can be sandwiched between the CNT grid and the silver film. The transition layer 323 can be a silicon dioxide layer having a thickness of about 20 nanometers. The silicon dioxide layer is deposited on a surface of the CNT grid. The silver film is deposited on a surface of the silicon dioxide layer opposite the CNT grid. The composite carbon nanotube film 32 including the CNT grid, the silicon dioxide layer, and the silver film can be defined as an Ag—SiO$_2$-CNT grid. If there are two metallic layers, a transition layer 323 can be deposited on two opposite surfaces of the CNT grid.

The Ag-CNT grid can be located on a surface of the detecting end to form an Ag-CNT probe. The Ag—SiO$_2$-CNT grid can be located on the surface of the detecting end to form an Ag—SiO$_2$-CNT probe. To test a Raman-enhancement capability of the Ag-CNT probe and the Ag—SiO$_2$-CNT probe, two organic molecules can be selected for measuring by the two probes.

Figure 13:
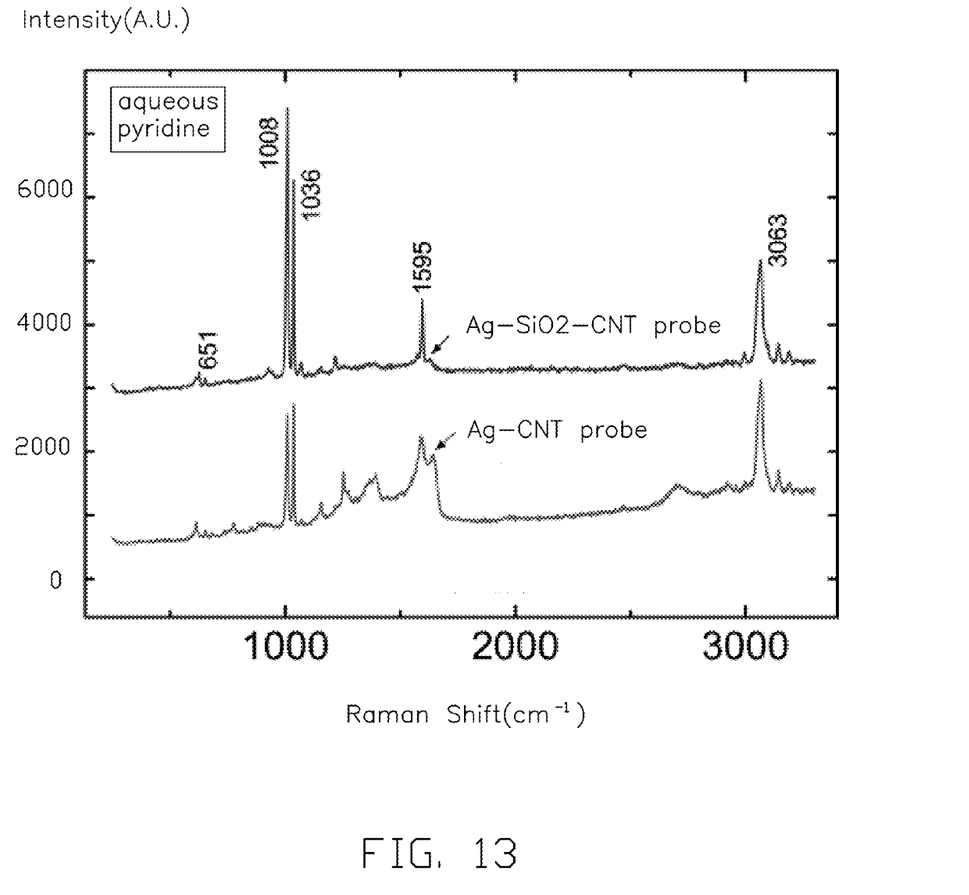
FIG. 13 shows a comparison of Raman spectra of aqueous pyridine on an Ag-CNT probe, and an Ag—SiO2-CNT probe.

The sample 200 including a water solution of pyridine (volume ratio of pyridine to water=1:4) can be applied to the Ag-CNT probe and the Ag—SiO$_2$-CNT probe and detected by the two probes. Raman spectra of the two probes can be recorded. As shown in FIG. 13, details and highly enhanced Raman peaks can be observed for pyridine adsorbed on the Ag-CNT probe and the Ag—SiO$_2$-CNT probe, and can reveal the capability of the two probes. The Raman peaks of the Ag—SiO$_2$-CNT probe are greater than the Raman peaks of the Ag-CNT probe.

Figure 14:
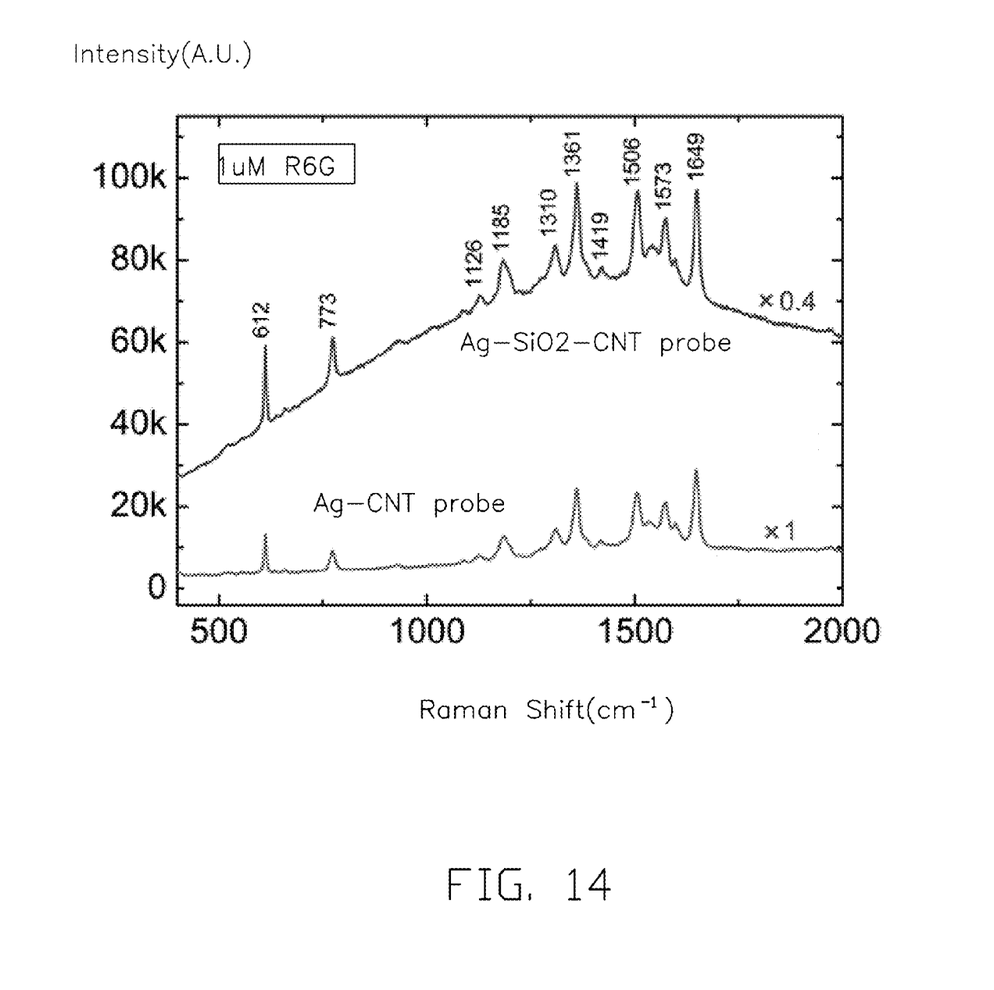
FIG. 14 shows comparison of Raman spectra of R6G on the two probes.

The sample 200 including a Rhodamine 6G (R6G) ethanol solution ($10^{-6}$ M) can be applied to the Ag-CNT probe and the Ag—SiO$_2$-CNT probe and detected by the two probes. Raman spectra of the R6G on the Ag-CNT probe and the Ag—SiO$_2$-CNT probe can be record after the evaporation of ethanol. As shown in FIG. 14, highly enhanced Raman peaks can be observed for R6G adsorbed on the Ag-CNT probe and the Ag—SiO$_2$-CNT probe. The Raman peaks of the Ag—SiO$_2$-CNT probe are greater than the Raman peaks of the Ag-CNT probe.

It is to be understood that the above-described embodiments are intended to illustrate rather than limit the disclosure. Any elements described in accordance with any embodiments is understood that they can be used in addition or substituted in other embodiments. Embodiments can also be used together. Vibrations may be made to the embodiments without departing from the spirit of the disclosure. The above-described embodiments illustrate the scope of the disclosure but do not restrict the scope of the disclosure.

What is claimed is:

1. An optical fiber probe, comprising:
 an optical fiber comprising a detecting end;
 a composite carbon nanotube film structure, located on a surface of the detecting end, wherein the composite carbon nanotube film structure comprises a carbon nanotube film structure, a metallic film, and a transition layer sandwiched between the carbon nanotube film structure and the metallic film, the carbon nanotube film structure comprises a plurality of carbon nanotubes joined by van der Waals attractive force therebetween;
 wherein the optical fiber probe is configured to detect Raman signals.

2. The optical fiber probe of claim 1, wherein the carbon nanotube film structure is wrapped around the detecting end.

3. The optical fiber probe of claim 1, wherein the carbon nanotube film structure is adhered to the surface of the detecting end by glue.

4. The optical fiber probe of claim 1, wherein the carbon nanotube film structure is adhered to the surface of the detecting end just by van der Waals attractive force.

5. The optical fiber probe of claim 1, wherein the carbon nanotube film structure is a free-standing structure that is wrapped around the detecting end.

6. The optical fiber probe of claim 1, wherein the plurality of carbon nanotubes are substantially perpendicular to the surface of the detecting end.

7. The optical fiber probe of claim 1, wherein the plurality of carbon nanotubes are substantially parallel to the surface of the detecting end.

8. The optical fiber probe of claim 7, wherein the carbon nanotube film structure comprises at least one carbon nanotube film, the plurality of carbon nanotubes of the at least one carbon nanotube film are substantially parallel to each other and joined end to end by the van der Waals attractive force therebetween.

9. The optical fiber probe of claim 8, wherein the carbon nanotube film structure comprises at least two layers of carbon nanotube films, wherein adjacent carbon nanotube films are adhered by the van der Waals attractive force therebetween.

10. The optical fiber probe of claim 9, wherein aligned directions of the plurality of carbon nanotubes of the adjacent drawn carbon nanotube films are substantially perpendicular to each other.

11. The optical fiber probe of claim 9, wherein the carbon nanotube film structure comprises at least four layers of carbon nanotube films.

12. A Raman detecting system, comprising:
 an optical fiber probe comprising an optical fiber, and a composite carbon nanotube film adhered to a detecting end of the optical fiber just by van der Waals attractive force;
 a projecting module configured to project a beam of light to the composite carbon nanotube film; and
 a receiving module configured to collect the beam of light that is scattered by the composite carbon nanotube film;
 wherein the composite carbon nanotube film comprises a carbon nanotube film structure, a metallic film and transition layer sandwiched between the carbon nanotube film structure and the metallic film.

13. The Raman detecting system of claim 12, wherein the detecting end is configured to receive the beam of light scattered by the composite carbon nanotube film and transmit the beam of light to the receiving module via the optical fiber.

14. The Raman detecting system of claim 12, wherein a measurement end of the optical fiber is configured to receive the beam of light and transmit the beam of light to the composite carbon nanotube film.

15. The optical fiber probe of claim 1, wherein a material of the transition layer is an inorganic oxide.

16. The optical fiber probe of claim 1, wherein a material of the transition layer is silicon dioxide or magnesium oxide.

17. The optical fiber probe of claim 1, wherein a thickness of the transition layer ranges from about 15 nanometers to about 30 nanometers.

18. The optical fiber probe of claim 1, wherein a thickness of the metallic film ranges from about 1 nanometer to about 45 nanometers.

19. The optical fiber probe of claim 18, wherein the thickness of the metallic film is about 5 nanometers.

* * * * *